United States Patent
Wang et al.

(10) Patent No.: US 12,233,159 B2
(45) Date of Patent: Feb. 25, 2025

(54) ASTAXANTHIN NANOEMULSION AND MANUFACTURING METHOD THEREOF

(71) Applicant: TRADE WIND BIOTECH CO., LTD., Taipei (TW)

(72) Inventors: Hui-Min Wang, Taichung (TW); Jui-Jen Chang, Kaohsiung (TW); Hsing-Yu Huang, Taichung (TW); Yi-Chen Wang, Taichung (TW)

(73) Assignee: Trade Wind Biotech Co., Ltd., Taipei (TW)

( * ) Notice: Subject to any disclaimer, the term of this patent is extended or adjusted under 35 U.S.C. 154(b) by 131 days.

(21) Appl. No.: 17/411,284

(22) Filed: Aug. 25, 2021

(65) Prior Publication Data
US 2023/0061072 A1    Mar. 2, 2023

(51) Int. Cl.
| | |
|---|---|
| *A61K 9/107* | (2006.01) |
| *A61K 31/122* | (2006.01) |
| *A61K 47/44* | (2017.01) |
| *B82Y 5/00* | (2011.01) |
| *B82Y 40/00* | (2011.01) |

(52) U.S. Cl.
CPC .......... *A61K 9/1075* (2013.01); *A61K 31/122* (2013.01); *A61K 47/44* (2013.01); *B82Y 5/00* (2013.01); *B82Y 40/00* (2013.01)

(58) Field of Classification Search
CPC .... A61K 9/1075; A61K 31/122; A61K 47/44; B82Y 5/00; B82Y 40/00
See application file for complete search history.

(56) References Cited

PUBLICATIONS

Huang Astaxanthin Nanoemulsion, Oxid. Med. & Cell. Longevity, p. 1 (Aug. 2020).*

* cited by examiner

*Primary Examiner* — Sarah Alawadi
*Assistant Examiner* — Thurman Wheeler
(74) *Attorney, Agent, or Firm* — Rosenberg, Klein & Lee

(57) ABSTRACT

The invention discloses an astaxanthin (AST) nanoemulsion and its manufacturing method. The manufacturing method comprising steps of: adding an AST material into a peanut oil and mixing them uniformly to obtain an AST oil; adding 0.25-1.5 (w/w) % of a surfactant into the AST oil and mixing them uniformly to obtain a mixed solution; and adding water into the mixed solution to obtain an AST emulsion precursor; and shaking the AST emulsion precursor to obtain the AST nanoemulsion.

6 Claims, 12 Drawing Sheets

ASTAXANTHIN NANOEMULSION AND MANUFACTURING METHOD THEREOF

BACKGROUND OF THE INVENTION

1. Field of the Invention

The present invention discloses an astaxanthin nanoemulsion and its manufacturing method, wherein the astaxanthin nanoemulsion is stable and bioavailable.

2. Description of Related Art

Astaxanthin (AST) is a xanthophyll carotenoid and is usually found in seafood, microorganisms or algae such as salmons, trouts, shrimps, lobsters, crabs and Chlorophyceae. AST has plural functions including anti-oxidation, anti-inflammatory, enhancement of immune response, anti-bacterial and anti-cancer. However, AST is limited in aquaculture, medicine, cosmetics, and functional food ingredient business applications due to its low stability in storage and poor solubility in the water phase.

SUMMARY OF THE INVENTION

The present invention discloses an astaxanthin (AST) nanoemulsion and its manufacturing method.

The manufacturing method of the present invention is achieved by the following steps, comprising:
(a) adding an AST material into a peanut oil and mixing them uniformly to obtain an AST oil; (b) adding 0.25-1.5 (w/w) % of a surfactant into the AST oil and mixing them uniformly to obtain a mixed solution; (c) adding water into the mixed solution to obtain an AST emulsion precursor; and (d) shaking the AST emulsion precursor to obtain the AST nanoemulsion.

In a preferred embodiment of the present invention, the step (b) is operated at 45° C.

In a preferred embodiment of the present invention, the AST emulsion precursor in the step (d) is shaken by an ultrasonicator.

In a preferred embodiment of the present invention, the surfactant is $_D$-α-tocopherol polyethylene glycol succinate (TPGS).

In a preferred embodiment of the present invention, the AST nanoemulsion comprises plural nano-droplets.

In a preferred embodiment of the present invention, a diameter of each of the plural nano-droplets ranges from 100 nm to 200 nm.

In a preferred embodiment of the present invention, the AST nanoemulsion comprises $8 \times 10^{-4}$–2 mg/mL of astaxanthin.

DETAILED DESCRIPTION OF THE PREFERRED EMBODIMENT

1. Preparation of Oil-In-Water Astaxanthin Nanoemulsion

*Haematococcus pluvialis* astaxanthin (AST) is used in this embodiment and is purchased from Tianbaoherb Biotech Co., Ltd. (Shanxi Province, China). The AST was dissolved in peanut oil and stirred at a room temperature for a period of time to obtain a first oil solution. The first oil solution was then filtered by a 0.45 μm membrane filter to remove undissolved AST and obtain an AST oil. Concentration of the AST in the AST oil is analyzed by measuring an absorbance of 450 nm thereof by a spectrophotometer.

$_D$-α-tocopherol polyethylene glycol succinate (TPGS) was added into in the AST oil at 0.25-1.5 (w/w) % and dissolved in the AST oil at 45° C. to obtain an uniformly mixed solution. 2.0 mL of deionized water was then added into the uniformly mixed solution, and then the uniformly mixed solution was shaken to nanosized scale by an ultrasonicator to obtain an oil in water AST nanoemulsion which is described as TAP-nanoemulsion in the following description.

2. Analyzation of the TAP-Nanoemulsion (1) Microstructure

Figure 1:
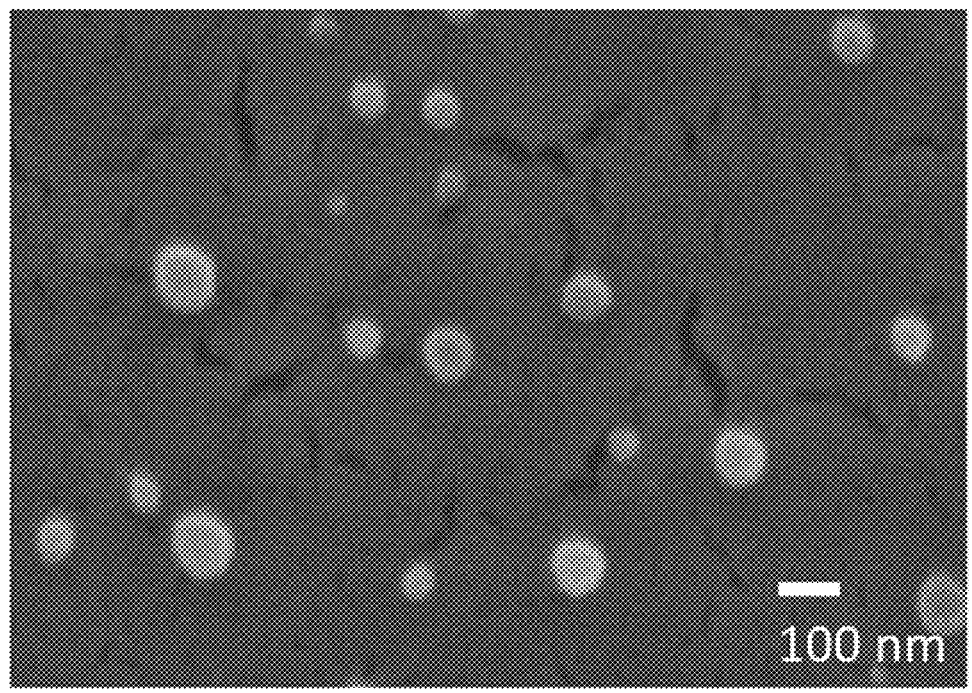
FIG. 1 is a microscopic photograph of the astaxanthin nanoemulsion of the present invention.

The microstructure of the TAP-nanoemulsion is observed by a Cryo-field emission scanning electron microscopy (Cryo-FESEM). A drop of the TAP-nanoemulsion was filled into brass rivets and frozen by liquid nitrogen. The frozen TAP-nanoemulsion was than observed by the Cryo-FESEM. Referring to FIG. 1, the TAP-nanoemulsion has a spherical shape in the nanometer scale.

(2) Droplet Size

The droplet size and size distribution of the TAP-nanoemulsion were measured by dynamic light scattering (DLS). The TAP-nanoemulsion was diluted with a buffer solution (1:100) before the analysis to avoid multiple scattering effects. Each sample was evaluated in triplicate.

Figure 2A:
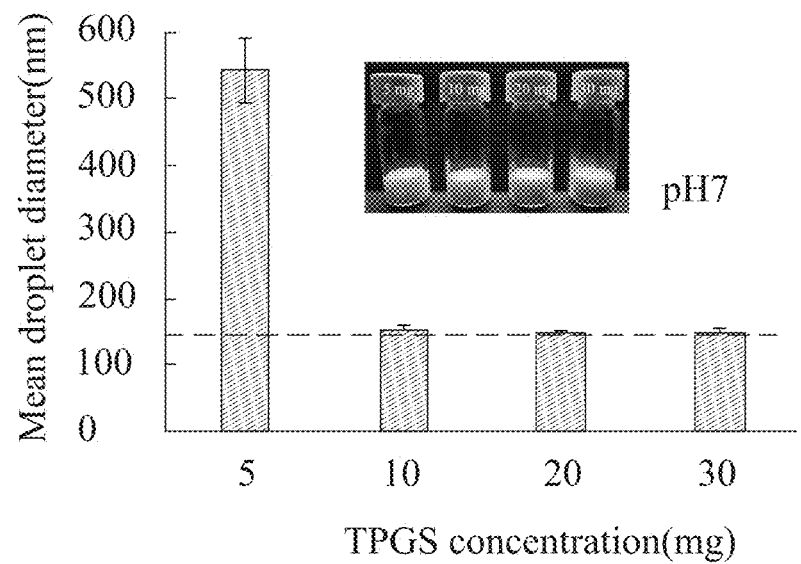
FIG. 2(A) is a bar graph showing a diameter of the astaxanthin nanoemulsion prepared with different amounts of TPGS in the present invention.

Referring to FIG. 2(A), the TAP-nanoemulsion prepared by adding 5 mg TPGS (0.25 (w/w) % TPGS) has the largest size distribution and a mean droplet diameter of 542.1 t 49.5 nm, and polydispersity index (PDI) thereof is 0.251. The TAP-nanoemulsion prepared by adding 10 mg TPGS (0.5 (w/w) % TPGS) has a PDI of 0.239 and a mean droplet diameter of 150.5±7.32 nm which is 3.5 times lower than the "5 mg TPGS" TAP-nanoemulsion. The mean droplet diameters of the TAP-nanoemulsion prepared by adding 20 mg TPGS (1.0 (w/w) % TPGS) and 30 mg TPGS (1.5% TPGS) were 155.0±40.8 nm and 145.6±27.7 nm, respectively. It suggested that the mean diameter of the TAP-nanoemulsion is decreased when the TPGS added is increased.

(3) Stability

Physical and chemical stabilities of a TAP-nanoemulsion prepared by 0.5 (w/w) % TPGS, 10 (w/w) % AST and 20 (w/w) % peanut oil were examined.

Figure 2B:
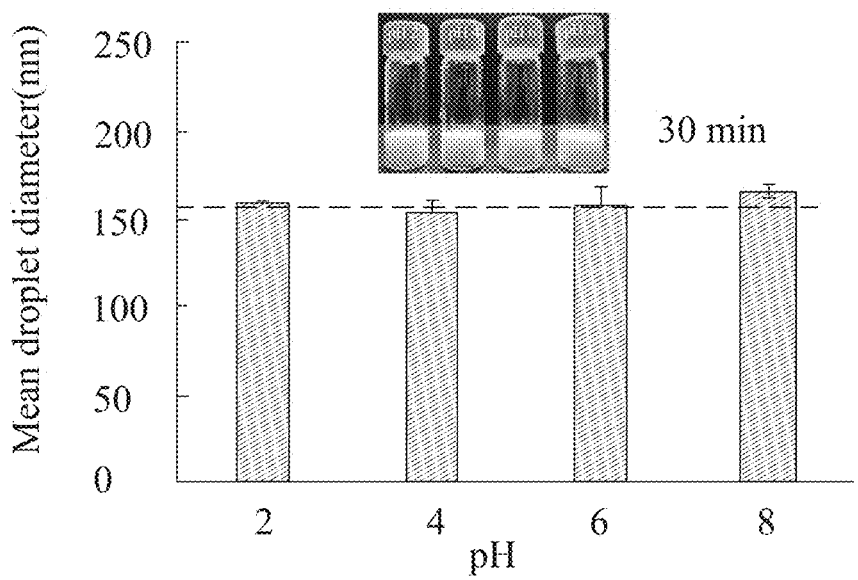
FIG. 2(B) is a bar graph showing a diameter of the astaxanthin nanoemulsion in the present invention stored in different pH value.

First, the TAP-nanoemulsion was added into a 5 mM phosphate buffer and the pH value thereof was adjusted to pH 2.0-8.0 by adding 0.1 mol/L HCl solution or 0.1 mol/L NaOH solution. The phosphate buffer containing the TAP-nanoemulsion was then stored at 25° C. for 1 day. After 1 day, the diameter of the TAP-nanoemulsion was analyzed by DLS. Referring to FIG. 2(B), the TAP-nanoemulsion prepared by 0.5 (w/w) % TPGS (10 mg TPGS) was stable in the solutions having different pH value, and the diameters of the droplets are constant about 150 nm. In addition, there was no phase segmentation phenomenon and the droplet aggregation in all samples. The diameter was a little increased when the TAP-nanoemulsion was incubated in the phosphate buffer of pH 8.0. In the pH 2.0 group and the pH 4.0 group, the diameters of the TAP-nanoemulsion were 154.0±8.6 nm and 155.3±4.9 nm respectively. The result suggested that the TAP-nanoemulsion is stable in pH 2.0-8.0, and especially in pH 2.0-6.0.

Second, ionic strength stability of the TAP-nanoemulsion was examined by the following method. The TAP-nanoemulsion was added in a sodium chloride (NaCl) solution (pH 7.0) and gently mixed for 30 seconds. The NaCl solution was then incubated at 5° C. for 24 hrs. The diameter of the TAP-nanoemulsion was then analyzed by DLS. NaCl can decrease the electrostatic repulsions between nano-particles of the TAP-nanoemulsion and make the TAP-nanoemulsion instable.

Figure 3A:
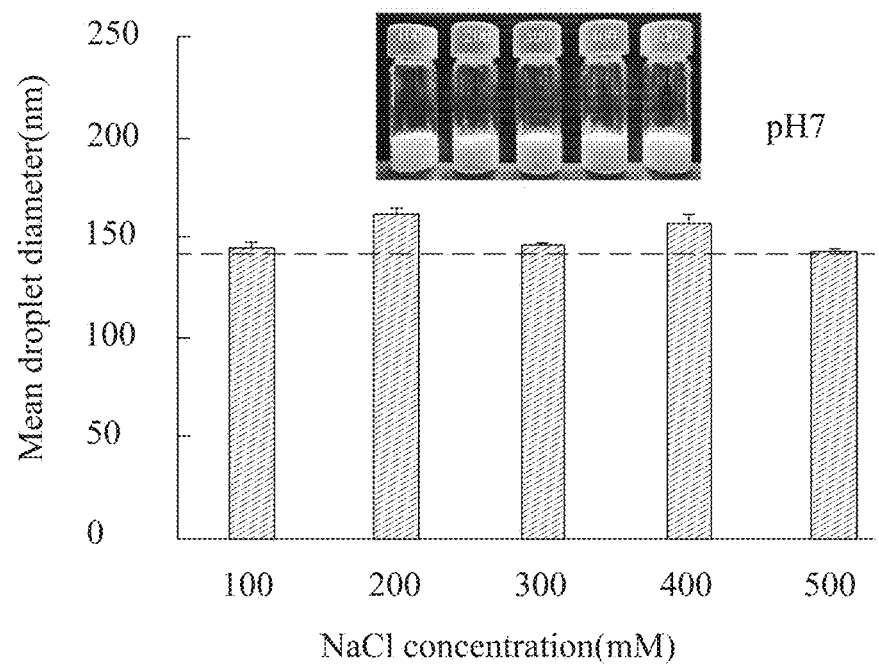
FIG. 3(A) is a bar graph showing a diameter of the astaxanthin nanoemulsion in the present invention stored in NaCl solution.

Referring to FIG. 3(A), the diameter of the TAP-nanoemulsion added in 500 mM NaCl solution is 143.8 t 0.7 nm (PDI: 0.144) and is similar to the diameter of the TAP-nanoemulsion added in 100 mM, 200 mM, 300 mM and 400 mM NaCl solution. It suggested that the spatial repulsive force of the TAP-nanoemulsion is strong enough to keep droplets steady in a high concentration NaCl solution.

Third, thermal stability of the TAP-nanoemulsion was examined. The TAP-nanoemulsion was incubated at 30° C., 60° C. and 90° C. for 1 hr by a water-bath tank. The TAP-nanoemulsion was then cooled to the room temperature and analyzed by DLS.

Figure 3B:
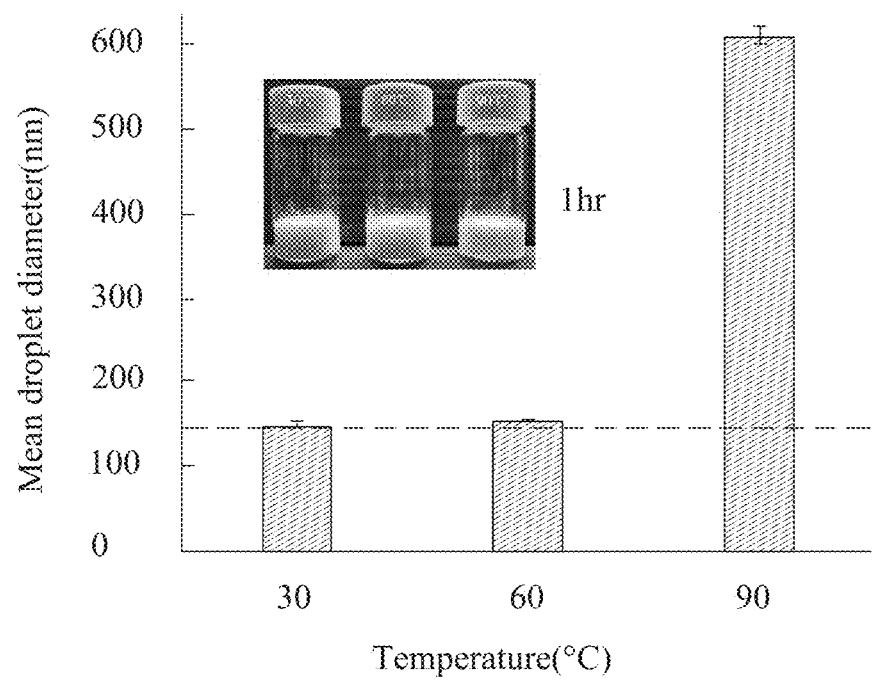
FIG. 3(B) is a bar graph showing a diameter of the astaxanthin nanoemulsion in the present invention stored in different temperature.

Referring to FIG. 3(B), the diameter of the TAP-nanoemulsion incubated at 30° C. is similar to the diameter incubated at 60° C. However, the diameter of the TAP-nanoemulsion incubated at 90° C. is significantly increased which suggested that the TAP-nanoemulsion is unstable at a high temperature. In addition, the color of the TAP-nanoemulsion incubated at 90° C. was orange-red, which indicated that astaxanthin was released from the TAP-nanoemulsion due to destruction of the TAP-nanoemulsion.

In addition, the concentration of AST in the TAP-nanoemulsion system was assayed by a UV-visible spectroscopy. AST was separated from the TAP-nanoemulsion droplet by solvent extraction and quantified by the UV-visible spectrophotometer. 9.8 mL of an organic solvent containing methanol:dichloromethane (1:2, v/v) was mixed with 0.2 mL of TAP-nanoemulsion, and the TAP-nanoemulsion was completely separated from the oil phase into an aqueous phase. The absorbance was measured at 470 nm, and the dichloromethane/methanol solution is used as a blank control.

3. Biofunctions of the TAP-Nanoemulsion (1) Cell Toxicity Assay

Cell toxicity of the TAP-nanoemulsion was determined by 3-(4,5-Dimethylthiazol-2-yl)-2,5-diphenyltetrazolium bromide (MTT) assay and the human foreskin fibroblast cells were used in this test. The cells were cultured with a density of $8 \times 10^3$ cells per well of a 96-well plate. After cultured for 1 day, cultured medium of the cells was replaced by fresh medium containing TPGS, peanut oil or the TAP-nanoemulsion. The cells were than incubated for another 24 hrs and cell viability was determined by MTT assay.

Figure 4A:
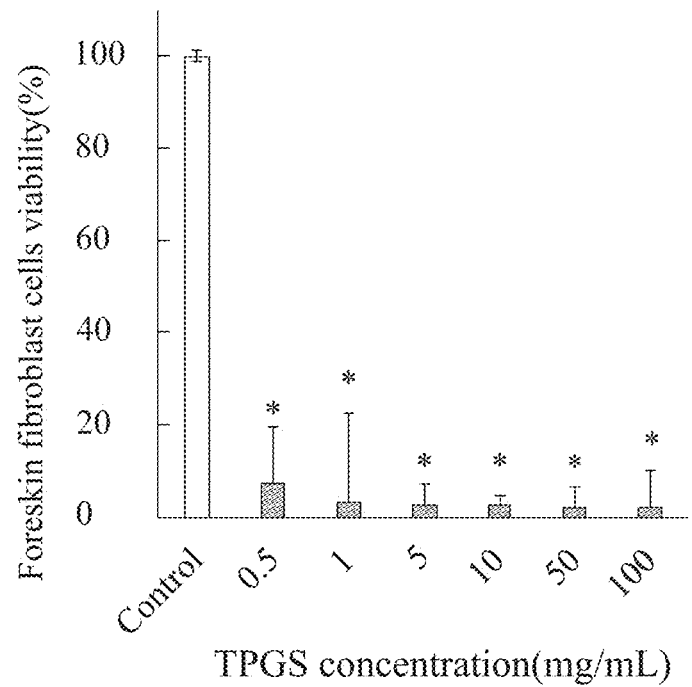
FIG. 4(A) is a bar graph showing cell viability of cell treated with TPGS.
Figure 4B:
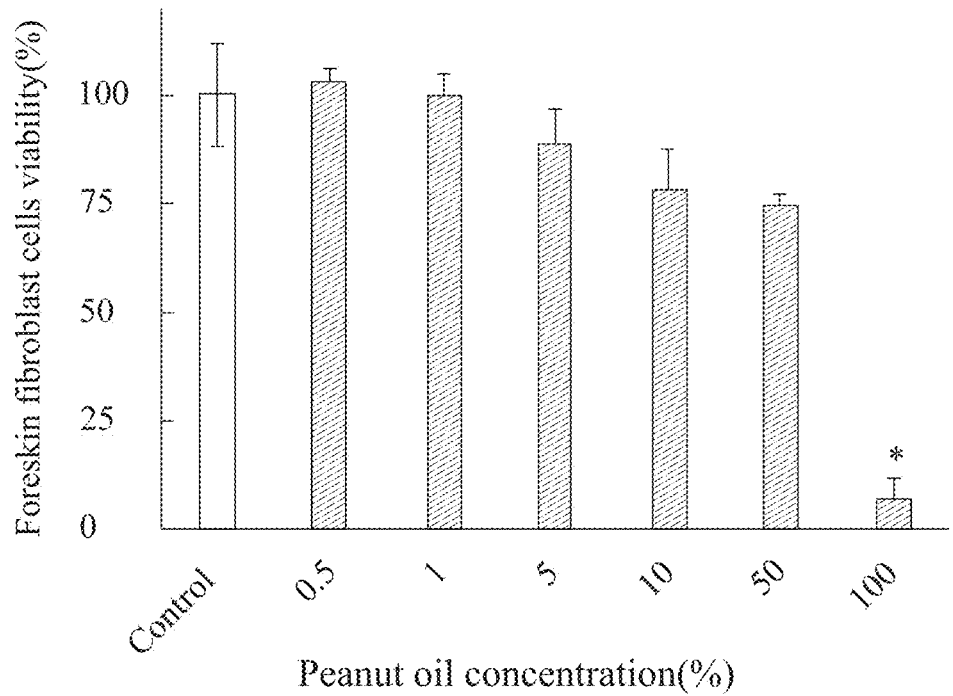
FIG. 4(B) is a bar graph showing cell viability of cells treated with peanut oil.

Referring to FIG. 4(A), the cell viability was less than 10% when the cells were treated with TPGS over 1 mg/mL, but it is normal because a surfactant may lyse cell membrane when directly incubating with the cells. Referring to FIG. 4(B), the cell viability is higher than 90% when the concentration of the peanut oil is lower than 50% (v/v). However, cell viability was significantly decreased when the cells were incubated in 100% (v/v) peanut oil.

Figure 5:
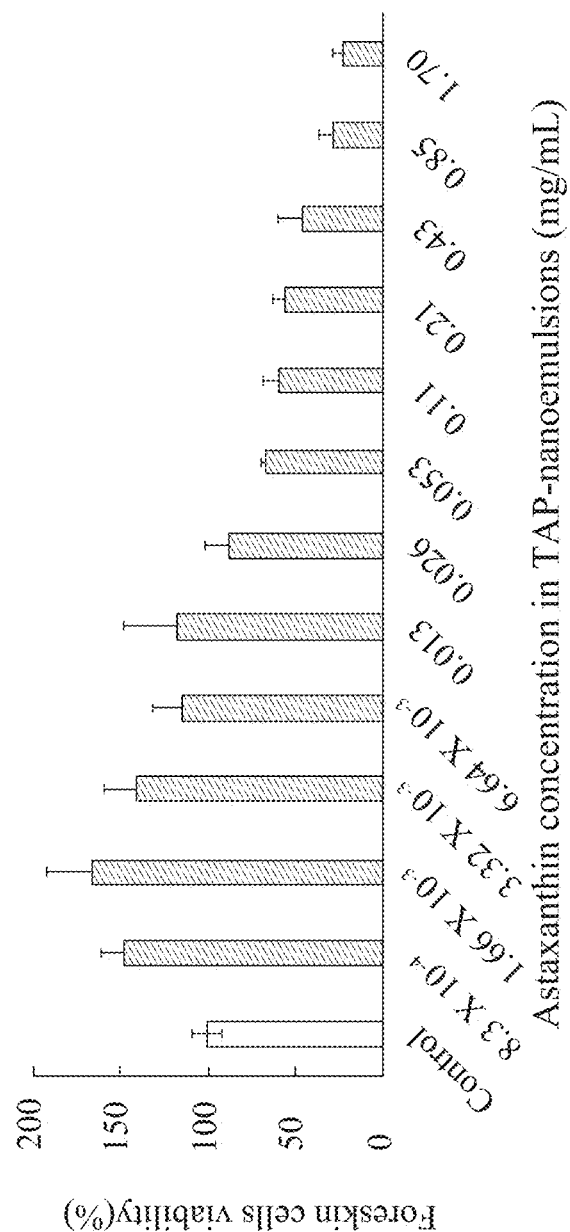
FIG. 5 is a bar graph showing cell viability of cells treated with TAP-nanoemulsion of the present invention.

Please referring to FIG. 5, the cell viability was increased in cells treated with the TAP-nanoemulsion containing $8.3 \times 10^{-4}$–0.013 mg/mL AST. And the cell viability was gradually decreased when the cells were treated with the TAP-nanoemulsion containing 0.053-1.7 mg/mL AST. Therefore, the highest concentration of AST in the TAP-nanoemulsion used in the following test is 0.053 mg/mL.

(2) Reactive Oxygen Species (ROS) in Cells Treated with the TAP-Nanoemulsion

The human foreskin fibroblast cells were pretreated with or without 0-26 μg/mL of the TAP-nanoemulsion for 24 hrs, and the cells were stimulated by 20 μg/mL phorbol 12-myristate 13-acetate (PMA) for another 24 hrs. The cells were incubated within a ROS-sensitive fluorescent dye, 2',7'-Dichlorofluorescin diacetate (DCFDA) for 30 min. The cellular fluorescence intensity in the cells was then analyzed by flow cytometry.

Figure 6:
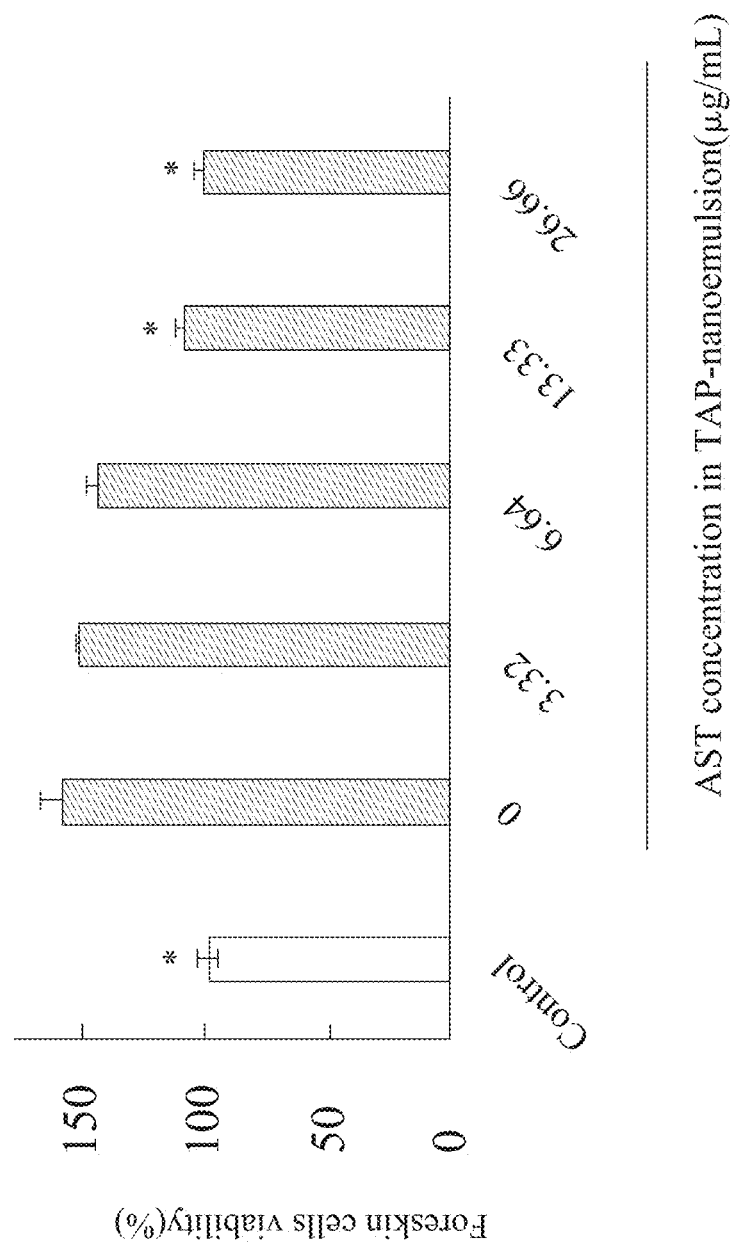
FIG. 6 is a bar graph showing ROS contents in cells treated with TAP-nanoemulsion of the present invention.

Referring to FIG. 6, ROS was increased in cells treated with PMA compared to the control group. ROS was gradually decreased in cells pretreated with TAP-nanoemulsion in a dose-dependent manner. The fluorescence potency of DCFDA was reduced from 159.35% to 101.00% in cells treated the TAP-nanoemulsion containing 0 μg/mL and 26.66 μg/mL AST respectively. This suggested that TAP-nanoemulsion inhibits production of ROS.

(3) TAP-Nanoemulsion Stability Under Simulated Gastric and Intestinal Fluid

A simulated gastric fluid was prepared by mixing 7.0 mL HCl, 2.0 g NaCl and water to obtain 1.0 L of the simulated gastric fluid whose pH value is 1.2. The simulated intestinal fluid was prepared by mixing 2.5 mL of pancreatic lipase solution (60 mg in PBS), 3.5 mL of bile extract (187.5 mg in PBS) and 1.5 mL of calcium chloride (110 mg in water) at pH 7.0, 37° C.

The TAP-nanoemulsion (2 mL) was added to a dialysis bag and immersed into the simulated gastrointestinal fluid maintained at 37° C. The simulated gastrointestinal fluid was stirred 100 rpm during the test. At a scheduled time point, 1.0 mL of the TAP-nanoemulsion was taken and analyzed, and a same volume of pre-warmed fresh PBS was added into the dialysis bag. The concentration of AST in the TAP-nanoemulsion was analyzed by HPLC, and the results are showed as a percentage of AST released amount over time.

Figure 7A:
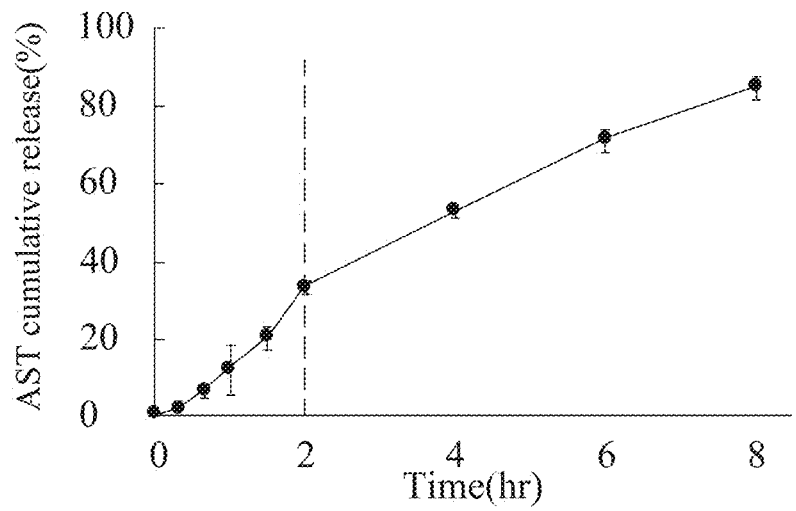
FIG. 7(A) is a line graph showing AST cumulative releasing rate of the TAP-nanoemulsion in the present invention.

Referring to FIG. 7(A), the AST gastrointestinal release profile exhibits two-stage drug discharge behaviors in a stomach and intestines. Initially, the AST releasing speed was slow and then speed up in the first phase. The released amount of AST was less than 35% within 2 hrs. In the second stage, the AST was slowly released in the simulated intestinal, and the release amount of AST reaches to 80% after 6 hrs.

(4) Permeability of TAP-Nanoemulsion

Furthermore, Caco-2 cells were used to analyze the cellular uptake of TAP-nanoemulsion in vitro. Caco-2 cells ($1\times10^5$ cells/2.4 $cm^2$ insert) were seeded in a transwell chamber (0.4 μm pore size, 24 mm diameter) at a density of $1\times10^5$ cells/2.4 $cm^2$ insert. The cell culture media were replaced by fresh medium every two days, until a monolayer of cells is observed. The monolayer cells were washed twice by with PBS (pH 7.4, 37° C.) and then cultured with the TAP-nanoemulsion overnight at 37° C. in 5% $CO_2$ atmosphere. The TAP-nanoemulsion was gently removed after incubation and the insert having monolayer of cells was loaded into a 6-well transwell plate. To analyze AST permeability, 0.5 mL of the TAP-nanoemulsion was added into the top side of the transwell plate (donor chamber). The basolateral chamber (receiving chamber) contains 0.5 mL of medium. The cells were cultured in a 5% $CO_2$ incubator for 24 hrs. After 24 hrs, the medium in the donor chamber and the receiving chamber were collected and the AST amount therein was analyzed by an UV-visible spectroscopy. The AST concentration in the TAP-nanoemulsion used in the embodiment comprises 1.66 μg/mL, 3.22 μg/mL, 6.64 μg/mL, 13.3 μg/mL, and 26.6 μg/mL.

Figure 7B:
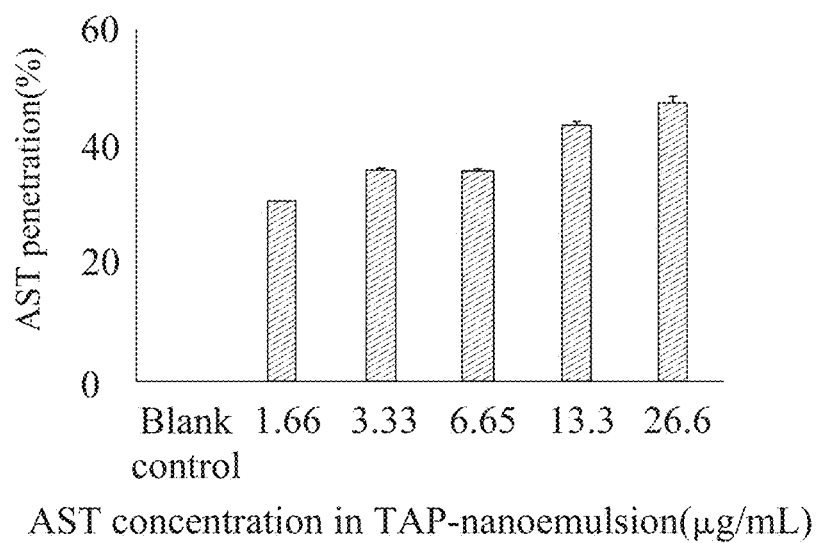
FIG. 7(B) is a bar graph showing AST penetration rate of the TAP-nanoemulsion in the present invention.

Referring to FIG. 7(B), the TAP-nanoemulsions can penetrate the monolayer cells efficiently and the AST penetration rate ranges from 30.7±0.04% (the "1.6 μg/mL AST" group) to 47.9±0.86% (the "26.6 μg/mL AST" group). The difference of the AST penetration rate may cause by AST metabolic conversion and chemical biodegradation during transepithelial infiltration. It suggested that the TAP-nanoemulsion of the present invention can be delivered through the epithelial layer by the passive transport.

(5) Inhibition of Metastasis of Melanoma

C57BL/6 female mice (6-7 weeks) were used in the embodiment to observe effect of the TAP-nanoemulsion on tumor growth and metastasis. The C57BL/6 mice were randomly divided into three groups: vehicle control group, tumor only group and TAP-nanoemulsion group.

The mice in the control group do not receive any treatment as a normal control. The melanoma cell line, B16F10 cells, were stained with fluorescent dye and then injected into the tail vein of the mice in the tumor only group and the TAP-nanoemulsion group twice a week, and $1\times10^5$ cells of B16F10 cells were injected to each mouse. Two weeks after tumor injection, each of the mice in the tumor only group receives 0.2 mL normal saline per day by oral gavage, and each of the mice in the TAP-nanoemulsion group receives 10 mg/Kg of the TAP-nanoemulsion per other day by an oral gavage.

After 35 days of receiving normal saline or the TAP-nanoemulsion, all mice were sacrificed, and the lung, spleen, heart, kidneys and liver organs were collected.

The body weights of all mice were recorded twice a week, and tumor growth was measured by IVIS spectral imaging system (Caliper Life Sciences, Hopkinton, MA, USA).

Figure 8A:
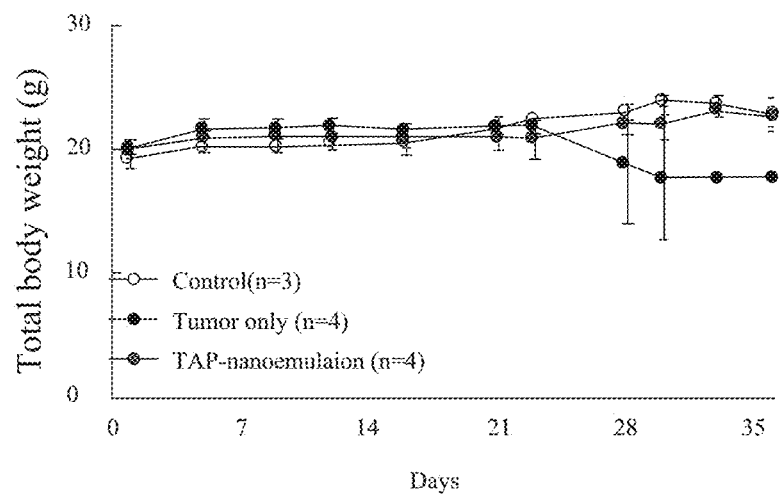
FIG. 8(A) is a line graph showing body weight of the mice.
Figure 8B:
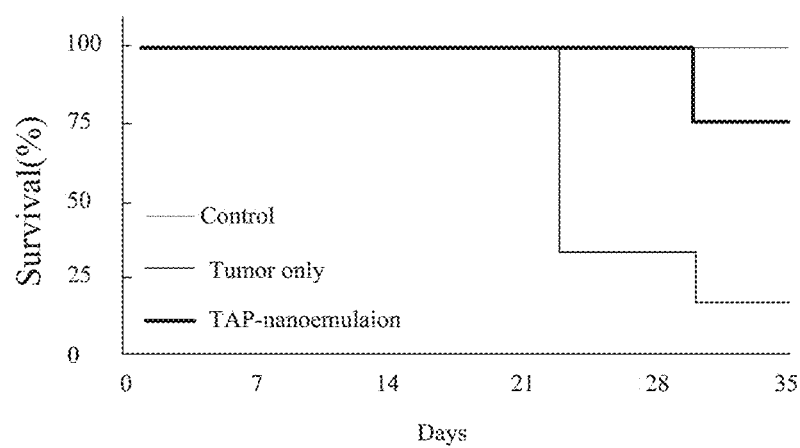
FIG. 8(B) is a line graph showing survival rate of the mice.

Referring to FIG. 8(A), the mice of the TAP-nanoemulsion group has a higher body weight than the mice in the tumor only group after 30 days of the experiment. Referring to FIG. 8(B), the mice of the TAP-nanoemulsion group also has a longer survival period and a higher survival rate than the tumor only group, only 1/4 mice died within 35 days of the TAP-nanoemulsion group.

Figure 9:
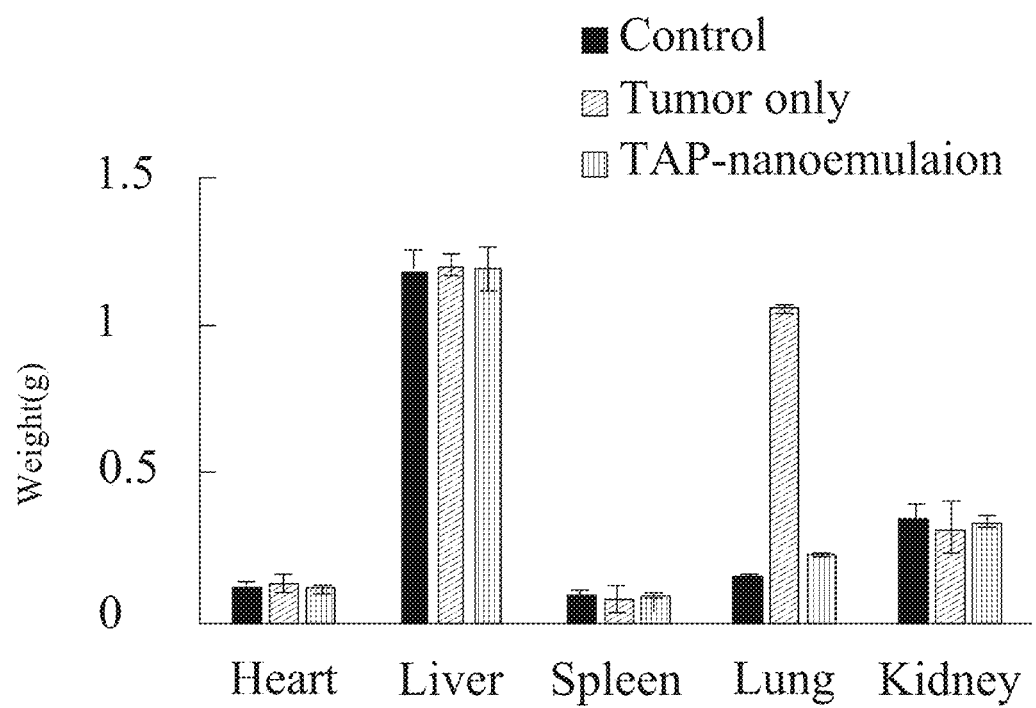
FIG. 9 is a bar graph showing weights of organs of the mice.

Referring to FIG. 9, the average lung weight of the mice in the tumor only group was 1.06±0.06 g, and the average lung weight of the mice in the TAP-nanoemulsion group was 0.25±0.05 g. The lung weight of the mice in the tumor only group is significantly higher than the TAP-nanoemulsion group due to lung metastatic melanoma tumor cells. In the TAP-nanoemulsion group, the metastatic melanoma cells in the lung were reduced significantly. The weights of the heart, liver, spleen and kidney are similar among the three groups, which suggested that the TAP-nanoemulsion has no toxicity to the mice.

Further, lung mRNA and lung protein of the mice in three groups were extracted and analyzed by real-time quantitative reverse transcription polymerase chain reaction (qRT-PCR) and Western blotting assay.

Figure 10:
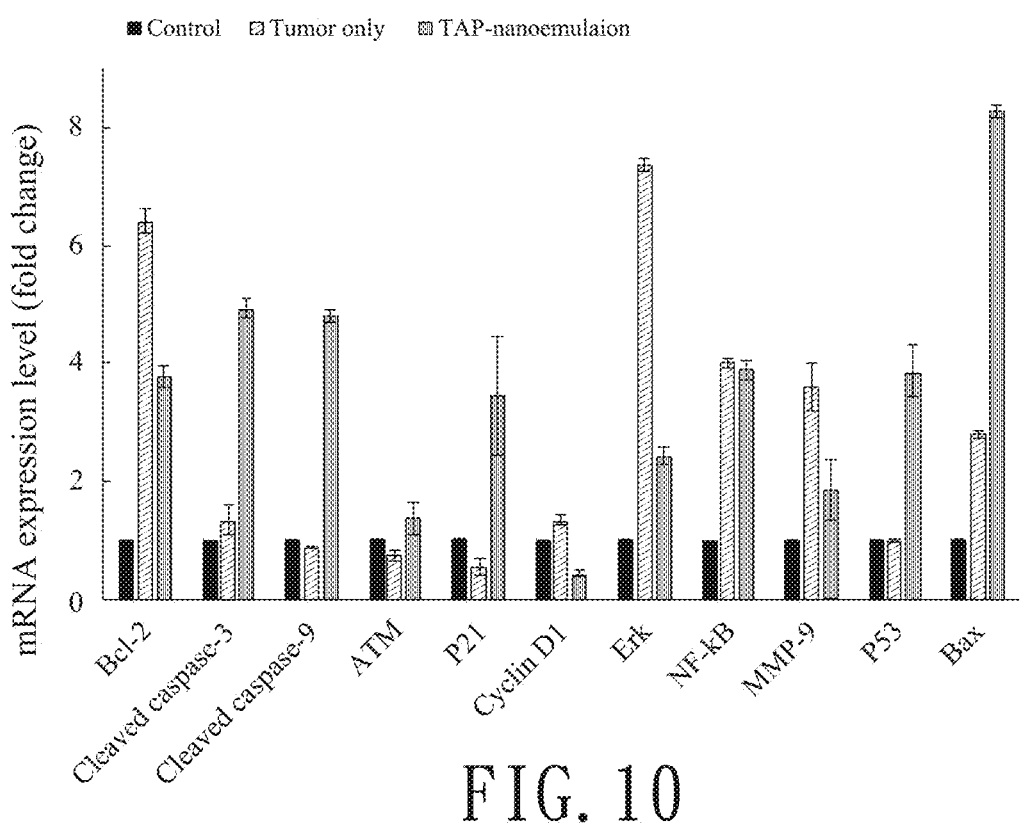
FIG. 10 is a bar graph showing mRNA expression of the lung of the mice.

Referring to FIG. 10, Bcl-2 mRNA was decreased in the TAP-nanoemulsion group compared to the tumor only group. Expression of the caspase-3 and caspase-9 mRNA which play important roles for cell apoptosis were increased in the TAP-nanoemulsion group. Expression of the ATM mRNA which controls cell growth and cell division was increased in the TAP-nanoemulsion group. Expression of cyclin-dependent kinase inhibitor p21 mRNA which triggers cell cycle arrest to stop at G1 phase and p53 was also increased in the TAP-nanoemulsion group. Further, expression of the cyc/in D/mRNA, extracellular signal-regulated protein kinase (ERK) mRNA, nuclear factor κ-light-chain-enhancer of activated B cell (NF-κB) mRNA, and matrix metalloproteinase-9 (MMP-9) mRNA were decreased in the TAP-nanoemulsion group compared to the tumor only group. It suggested that the TAP-nanoemulsion group induces apoptosis and reduces metastasis of the melanoma cells.

Figure 11A:
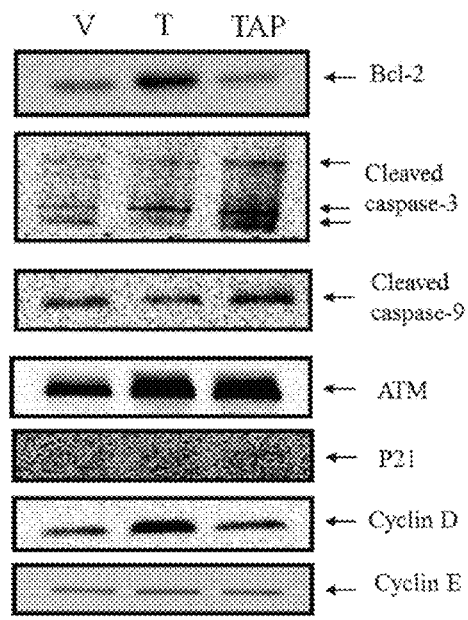
FIG. 11(A) is a photograph showing expression of cell death related proteins.
Figure 11B:
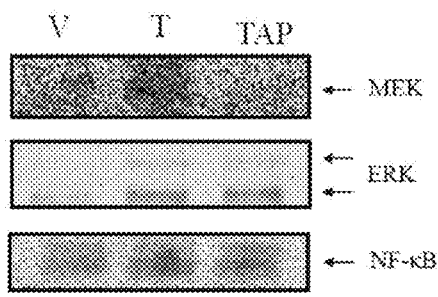
FIG. 11(B) is a photograph showing expression of signaling transduction related proteins.
Figure 11C:
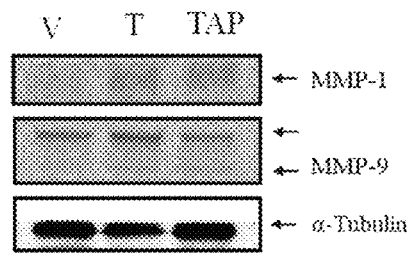
FIG. 11(C) is a photograph showing expression of metastasis related proteins.

Referring FIG. 11(A) to FIG. 11(C), protein expression of Bcl-2, cyclin D, ERK, NF-κB and MMP-9 in the TAP-nanoemulsion group (TAP) were decreased compared to the tumor only group (T). Protein expression of cyclin E, MEK and MMP-1 were also reduced in the TAP-nanoemulsion group (TAP).

Figure 12A:
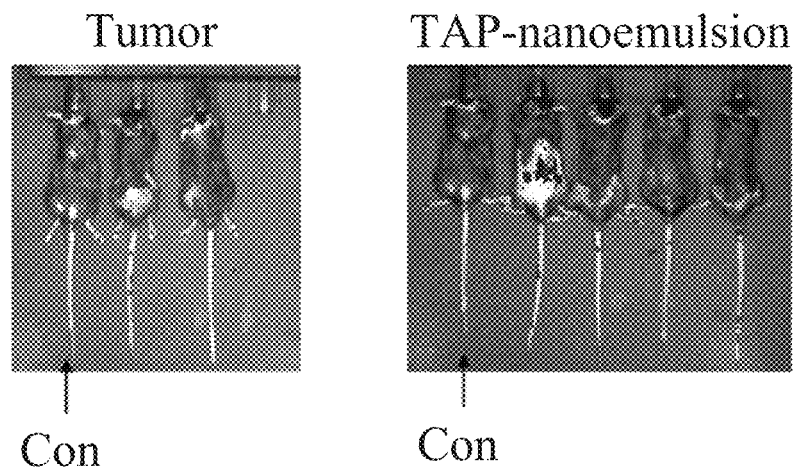
FIG. 12(A) is a photograph showing mice injected with tumor cells before receiving TAP-nanoemulsion.
Figure 12B:
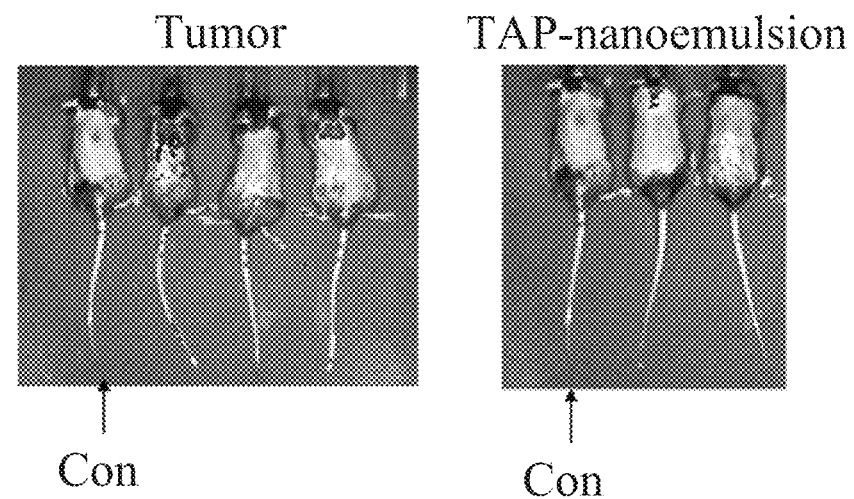
FIG. 12(B) is a photograph showing mice injected with tumor cells after receiving TAP-nanoemulsion.

FIG. 12(A) to FIG. 12(B) show graphs obtained by the IVIS spectral imaging system for observation of tumor growth of the mice. Referring to FIG. 12(A), before receiving normal saline or TAP-nanoemulsion, tumor cells (red areas) were observed in mice of the tumor only group and the TAP-nanoemulsion group, but there is no tumor cells observed of the mouse in the control group (marked by "Con"). Referring to FIG. 12(B), the volume of the tumor cells were reduced in the TAP-nanoemulsion group.

Accordingly, the present invention provides an astaxanthin nanoemulsion (TAP-nanoemulsion) and its manufacturing method. The TAP-nanoemulsion has a small diameter and has better physicochemical stability and bioavailability.

What is claimed is:

1. A manufacturing method of an astaxanthin (AST) nanoemulsion, comprising steps of:
   (a) adding an AST material into a peanut oil and mixing them uniformly to obtain an AST oil mixture;
   (b) adding 0.25-1.5 (w/w) % of D-α-tocopherol polyethylene glycol succinate (TPGS) into the AST oil mixture and mixing them uniformly to obtain a mixed solution;
   (c) adding water into the mixed solution to obtain an AST nanoemulsion precursor; and
   (d) shaking the AST nanoemulsion precursor to obtain the AST nanoemulsion.

2. The manufacturing method as claimed in claim 1, wherein the step (b) is operated at 45° C..

3. The manufacturing method as claimed in claim 1, wherein the AST nanoemulsion precursor in the step (d) is shaken by an ultrasonicator.

4. The manufacturing method as claimed in claim 1, wherein the AST nanoemulsion comprises nano-droplets.

5. The manufacturing method as claimed in claim 4, wherein a diameter of each of the nano-droplets ranges from 100 nm to 200 nm.

6. The manufacturing method as claimed in claim 1, wherein the AST nanoemulsion comprises $8\times10^{-4}$–2 mg/mL of astaxanthin.

* * * * *